United States Patent [19]

Atwal

[11] Patent Number: 4,684,656
[45] Date of Patent: Aug. 4, 1987

[54] 1,2,3,4-TETRAHYDRO-6-SUBSTITUTED-4-ARYL-3-(SUBSTITUTED SULFONYL)-2-THIOXO(OR OXO)-5-PYRIMIDINECARBOXYLIC ACIDS AND ESTERS AND METHOD OF USING THEM TO LOWER BLOOD PRESSURE

[75] Inventor: Karnail Atwal, Cranbury, N.J.

[73] Assignee: E. R. Squibb & Sons, Inc., Princeton, N.J.

[21] Appl. No.: 840,130

[22] Filed: Mar. 14, 1986

[51] Int. Cl.$^4$ ............... A61K 31/505; C07D 239/22
[52] U.S. Cl. ........................................ 514/274; 544/2; 544/3; 544/5; 544/7; 544/8; 544/55; 544/58.1; 544/58.5; 544/58.6; 544/63; 544/65; 544/66; 544/67; 544/72; 544/82; 544/96; 544/111; 544/112; 544/113; 544/114; 544/120; 544/121; 544/122; 544/123; 544/179; 544/180; 544/182; 544/238; 544/295; 544/296; 544/316; 544/318
[58] Field of Search ............... 544/316, 318; 514/274

[56] References Cited

U.S. PATENT DOCUMENTS 4,532,248 7/1985 Franckowiak et al. ............ 514/302
4,609,494 9/1986 Baldwin et al. .................... 544/250

FOREIGN PATENT DOCUMENTS 157219 10/1985 European Pat. Off. ............ 514/274
3234684 3/1984 Fed. Rep. of Germany ...... 544/316
868030 5/1961 United Kingdom ................ 514/274

OTHER PUBLICATIONS

Rutter et al., Chem. Abst., 49, 14769i, (1955).
McKinstry et al., Chem. Abst., 38, 26534, (1944).
McKinstry et al., Chem. Abst., 38, 43184, (1944).
*Medicinal Chemistry*, Burger Edit., 2nd Ed., 1960, pp. 565-571, 579-581, 600, and 601.
Khanina et al., Khim. Farm Zh., vol. 12, pp. 1321-1322, (1978), "Synthesis and Pharmacological Investigation . . .".
Konyukhov et al., Zh. Organ. Khim., vol. 1, No. 8, pp. 1487-1489, (1965), "Synthesis and Investigation . . .".
Elkasaby, Pakistan J. Sci. Ind. Res., vol. 21, No. 2, pp. 58-61, (1978), "Condensation of Ethyl α-Acetylcinnametes with Thioureas".
George et al., Synthesis, (1975), pp. 405-407, "Condensed Heterocycles from 5-Ethoxycarbonyl-6-methyltetrahydropyrimidin-2-ones".
Folkers et al., J. Am. Chem. Soc., vol. 56, pp. 1374-1377, (1934), "Researches on Pyrimidines . . .".
J. Org. Chem., vol. 50, pp. 4227-4230, "Synthesis of Novel Dihydropyrimidines and Tetrahydropyrimidines", Cho et al., (1985).

*Primary Examiner*—John M. Ford
*Assistant Examiner*—Kurt G. Briscoe
*Attorney, Agent, or Firm*—Lawrence S. Levinson; Donald J. Barrack

[57] ABSTRACT

Cardiovascular activity is exhibited by compounds having the formula

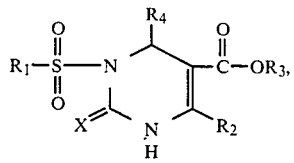

and pharmaceutically acceptable salts thereof wherein
X is oxygen or sulfur;
$R_1$ is alkyl, cycloalkyl, aryl, heterocyclo, —$(CH_2)_n$—$Y_1$, or halo substituted alkyl;
$R_2$ is hydrogen, alkyl, alkenyl, alkynyl, cycloalkyl, aryl, —$(CH_2)_n$—$Y_1$, or halo substituted alkyl;
$R_3$ is hydrogen, alkyl, cycloalkyl, aryl, heterocyclo, —$(CH_2)_n$—$Y_2$, —$(CH_2)_p$—$Y_3$, or halo substituted alkyl;
$R_4$ is aryl or heterocyclo;
$Y_1$ is cycloalkyl, aryl, heterocyclo, hydroxyl, alkoxy, aryl—$(CH_2)_m$—O—, mercapto, alkylthio, aryl—$(CH_2)_m$—S—, amino, substituted amino, carbamoyl, $$\text{(substituted amino)}-\overset{\text{O}}{\underset{\|}{\text{C}}}-,\ \text{heterocyclo}-(CH_2)_m-\overset{\text{O}}{\underset{\|}{\text{C}}}-,\ \text{carboxyl,}$$

$$\text{alkoxycarbonyl, alkyl}-\overset{\text{O}}{\underset{\|}{\text{C}}}-,\ \text{aryl}-(CH_2)_m-\overset{\text{O}}{\underset{\|}{\text{C}}}-,$$

$$\text{alkyl}-\overset{\text{O}}{\underset{\|}{\text{C}}}-\text{O}-\ \text{or aryl}-(CH_2)_m-\overset{\text{O}}{\underset{\|}{\text{C}}}-\text{O}-;$$

$Y_2$ is cycloalkyl, aryl, heterocyclo, carbamoyl, $$\text{(substituted amino)}-\overset{\text{O}}{\underset{\|}{\text{C}}}-,\ \text{carboxyl, alkoxycarbonyl, alkyl}-\overset{\text{O}}{\underset{\|}{\text{C}}}-,$$

$$\text{aryl}-(CH_2)_m-\overset{\text{O}}{\underset{\|}{\text{C}}}-\ \text{or heterocyclo}-(CH_2)_m-\overset{\text{O}}{\underset{\|}{\text{C}}}-;$$

$Y_3$ is hydroxyl, alkoxy, aryl—$(CH_2)_m$—O—, mercapto, alkylthio, aryl—$(CH_2)_m$—S—, $$\text{alkyl}-\overset{\text{O}}{\underset{\|}{\text{C}}}-\text{O}-,\ \text{aryl}-(CH_2)_m-\overset{\text{O}}{\underset{\|}{\text{C}}}-\text{O}-,$$

amino, or substituted amino;
m is 0 or an integer of 1 to 6;
n is an integer of 1 to 6;
p is an integer of 2 to 6.

21 Claims, No Drawings

1,2,3,4-TETRAHYDRO-6-SUBSTITUTED-4-ARYL-3-(SUBSTITUTED SULFONYL)-2-THIOXO(OR OXO)-5-PYRIMIDINECARBOXYLIC ACIDS AND ESTERS AND METHOD OF USING THEM TO LOWER BLOOD PRESSURE

BRIEF DESCRIPTION OF THE INVENTION

Compounds having the formula

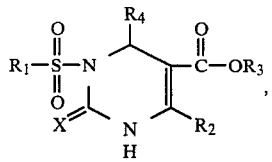

I and pharmaceutically acceptable salts thereof, are cardiovascular agents. In formula I, and throughout the specification, the symbols are as defined below.

X is oxygen or sulfur;

$R_1$ is alkyl, cycloalkyl, aryl, heterocyclo, —$(CH_2)_n$—$Y_1$, or halo substituted alkyl;

$R_2$ is hydrogen, alkyl, alkenyl, alkynyl, cycloalkyl, aryl, —$(CH_2)_n$—$Y_1$, or halo substituted alkyl;

$R_3$ is hydrogen, alkyl, cycloalkyl, aryl, heterocyclo, —$(CH_2)_n$—$Y_2$, —$(CH_2)_p$—$Y_3$, or halo substituted alkyl;

$R_4$ is aryl or heterocyclo;

$Y_1$ is cycloalkyl, aryl, heterocyclo, hydroxyl, alkoxy, aryl—$(CH_2)_m$—O—, mercapto, alkylthio, aryl—$(CH_2)_m$—S—, amino, substituted amino, carbamoyl,

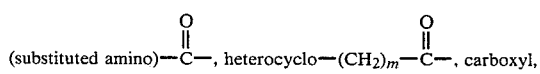

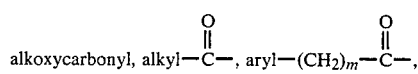

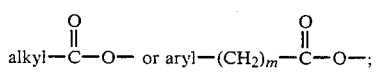

$Y_2$ is cycloalkyl, aryl, heterocyclo, carbamoyl,

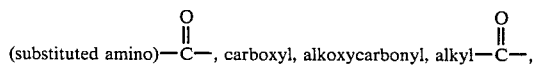

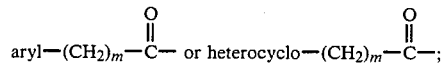

$Y_3$ is hydroxyl, alkoxy, aryl—$(CH_2)_m$—O—, mercapto, alkylthio, aryl-$(CH_2)_m$-S —

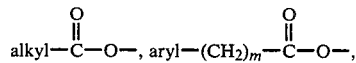

amino, or sutstituted amino;

m is 0 or an integer of 1 to 6;

n is an integer of 1 to 6; and p is an integer of 2 to 6.

Listed below are definitions of various terms used to describe the compounds of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 8 carbon atoms are preferred.

The term "halo substituted alkyl" refers to alkyl groups (as described above) in which one or more hydrogens have been replaced by chloro, bromo or fluoro groups. Exemplary groups are trifluoromethyl, methyl, which is preferred, pentafluoroethyl, 2, 2, 2-trichloroethyl, chloromethyl, bromomethyl, etc.

The term "aryl" refers to phenyl and substituted phenyl. Exemplary substituted phenyl groups are phenyl groups substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups.

The terms "alkenyl" and "alkynyl" refer to both straight and branched chain groups. Those groups having 2 to 8 carbon atoms are preferred.

The term "cycloalkyl" refers to those groups having 3, 4, 5, 6 or 7 carbon atoms.

The term "halo" refers to chloro, bromo, fluoro and iodo.

The term "heterocyclo" refers to fully saturated or unsaturated rings of 5 or 6 atoms containing one or two oxygen or sulfur atoms and/or one to four nitrogen atoms provided that the total number of hetero atoms in the ring is 4 or less. The heterocyclo ring is attached by way of an available carbon atom. Preferred monocyclic heterocyclo groups include 2- and 3-thienyl, 2- and 3-furyl, 2- and 3-pyrrolyl, 2-, 3- and 4-pyridyl, 2-, 4- and 5-imidazolyl, 2- and 3-pyrrolidinyl, 2-, 3- and 4-piperidinyl, and 2-, 3- and 4-azepinyl. The term heterocyclo also includes bicyclic rings wherein the five or six membered ring containing oxygen, sulfur and nitrogen atoms as defined above is fused to a benzene ring and the bicyclic ring is attached by way of an available carbon atom in the benzene ring. Preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6 or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

The term heterocyclo also includes such monocyclic and bicyclic rings as defined above substituted with one, or more, alkyl, arylalkyl, diarylalkyl, alkylthio, alkoxy, halo, nitro, oxo, cyano, hydroxy, amino, alkylamino, dialkylamino, trifluoromethyl, isocyanato, isothiocyanato or difluoromethoxy groups.

The term "substituted amino" refers to a group of the formula —$NZ_1Z_2$ wherein $Z_1$ is hydrogen, alkyl, or aryl—$(CH_2)_m$—and $Z_2$ is alkyl or aryl—$(CH_2)_m$—or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

DETAILED DESCRIPTION OF THE INVENTION

The compounds of formula I, and the pharmaceutically acceptable salts thereof, are cardiovascular agents. They act as calcium entry blocking vasodilators and are especially useful as hypotensive agents. Thus, by the administration of a composition containing one (or a combination) of the compounds of this invention, the blood pressure of a hypertensive mammalian (e.g., human) host is reduced. A single dose, or two to four divided daily doses, provided on a basis of about 0.1 to 100 milligrams per kilogram of body weight per day, preferably from about 1 to about 50 milligrams per kilogram per day, is appropriate to reduce blood pressure. The substance is preferably administered orally, but parenteral routes such as the subcutaneous, intramuscular or intravenous routes can also be employed.

As a result of the calcium entry blocking activity of the compounds of formula I, and the pharmaceutically acceptable salts thereof, it is believed that such compounds in addition to being hypotensive agents may also be useful as antiarrhythmic agents, anti-anginal agents, antifibrillatory agents, anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is sulfur can be prepared by reacting a keto ester compound having the formula

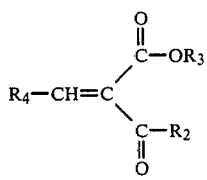

II with an S-(phenylmethyl)thiopseudourea having the formula

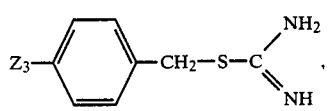

III or a salt thereof. In formula III, and throughout the specification, $Z_3$ is hydrogen or methoxy. The reaction mixture is heated in the presence of sodium acetate to yield a tautomeric mixture of compounds having the formulas

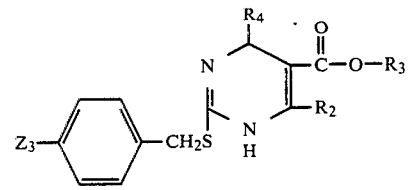

IV

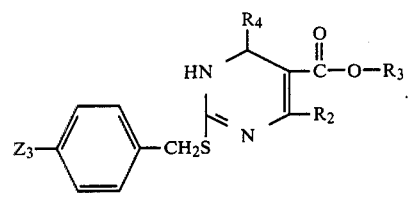

Reaction of a tautomeric mixture of formula IV with a sulfonyl chloride having the formula

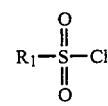

V in the presence of an organic base yields the corresponding compound having the formula

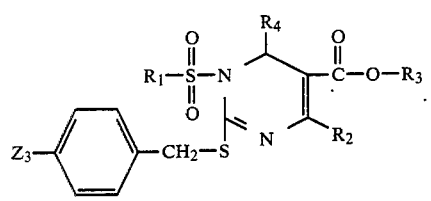

VI

A compound of formula VI wherein $Z_3$ is hydrogen can be converted to the corresponding product of formula I wherein X is sulfur by treatment with bromotrimethylsilane. A compound of formula VI wherein $Z_3$ is methoxy can be converted to the corresponding product of formula I wherein X is sulfur by treatment with trifluoroacetic acid and ethanethiol.

The compounds of formula I wherein X is oxygen can be prepared by heating a keto ester of formula II with

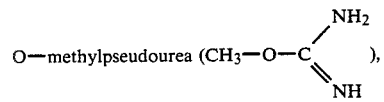

or a salt thereof, in the presence of sodium acetate or sodium bicarbonate to yield a tautomeric mixture of compounds having the formulas

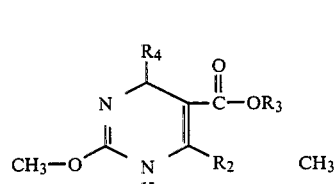

VII

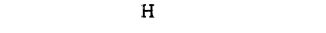

Reaction of a tautomeric mixture of formula VII with a sulfonyl chloride of formula V in the presence of an organic base yields the corresponding compound having the formula

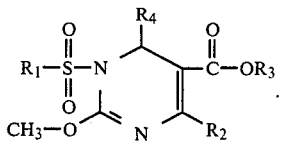

A compound of formula VIII can be converted to the corresponding product of formula I wherein X is oxygen by treatment with hydrochloric acid.

In those instances wherein the reactants described above contain reactive substituents not meant to participate in the reaction, it may be necessary to first protect these functional groups, carry out the desired reaction, and then remove the protecting group.

The compounds of formula I that contain a basic or acid group form acid addition and basic salts with a variety of inorganic and organic acids and bases. The pharmaceutically acceptable salts are preferred, although other salts may also be useful in isolating or purifying the product. Such pharmaceutically acceptable acid addition salts include those formed with hydrochloric acid, methanesulfonic acid, toluenesulfonic acid, sulfuric acid, acetic acid, maleic acid, etc. Pharmaceutically acceptable basic salts include alkali metal salts (e.g., sodium, potassium and lithium) and alkaline earth metal salts (e.g., calcium and magnesium). The salts can be obtained by reacting the product with an equivalent amount of the acid in a medium in which the salt precipitates.

Preferred compounds of this invention are those wherein:

$R_2$ is alkyl (especially methyl), $R_3$ is alkyl (especially ethyl) and $R_4$ is 3-nitrophenyl.

The following examples are specific embodiments of this invention.

EXAMPLE 1 1, 2, 3, 4-Tetrahydro-6-methyl-3-(methylsulfonyl)-4-(3-nitrophenyl)-2-thioxo-5-pyrimidinecarboxylic acid, methyl ester (A) S-(4-Methoxybenzyl)-S-thiopseudourea, hydrochloride A suspension of thiourea (38 g, 50.0 mmole) in dry tetrahydrofuran (40 ml) was cooled to 0° C. under argon and was treated dropwise with 4-methoxybenzyl-chloride (8.0 g, 50.0 mmole). After the addition was completed, the cooling bath was removed and the reaction was allowed to stir at room temperature for 2 hours. It was then heated at 60-65° C. for 4 hours whereupon a colorless voluminous precipitate was formed. The reaction was allowed to cool down to room temperature and was, diluted with anhydrous ether. The solid was filtered off and washed with anhydrous ether to give 10.92 g of 2-(4-methoxybenzyl)-2-thiopseudourea, hydrochloride, melting point 161–163.5° C. Analysis Calc'd. for $C_9H_{12}N_2OS\cdot HCl$: C, 46.45; H, 5.63; N, 12.04; S, 13.78; Cl, 15.23. Found: C, 46.48; H, 5.64; N, 12.25; S, 13.74; Cl, 15.31.

(B) 1, 4-Dihydro-2-[[(4-methoxyphenyl)methyl]thio]-6-methyl-4-(3-nitrophenyl) -5-pyrimidinecarboxylic acid, methyl ester A solution of 2-[(3-nitrophenyl)methylene]-3-oxobutanoic acid, methyl ester (5.0 g, 0.02 mole). in 20 ml of dimethylformamide under argon at room temperature was treated with S-(4-methoxybenzyl)-S-thiopseudourea, hydrochloride (4.65 g, 0.02 mole) and sodium acetate (1.64 g, 0.02 mole). The mixture was then heated at 65±5° C. for 3 hours. Upon cooling, ethyl acetate was added and a small amount of solids were filtered. The filtrate was washed with water (twice), aqueous sodium bicarbonate and saturated brine. The aqueous washes were extracted with fresh ethyl acetate. The combined filtrate and washings were dried (magnesium sulfate) and concentrated in vacuo to give about 9 g of crude product. Crystallization from acetone-isopropyl ether gave 6.8 g of product, melting point 125°–127.5° C., tlc, silica gel, ethyl acetate/hexane (1:1), $R_f=0.48$. Analysis Calc'd. for $C_{21}H_{21}N_3O_5S$: C, 59.00; H, 4.95; N, 9.83; S, 7.50. Found: C, 58.86; H, 4.82; N, 9.51; S, 7.25.

(C) 1, 6-Dihydro-2-[[(4-methoxyphenyl)methyl]thio]-4-methyl -1-(methylsulfonyl)-6-(3-nitrophenyl)-5-pyrimidinecarboxylic acid, methyl ester A solution of 1, 4-dihydro-2-[[(4-methoxyphenyl)methyl]thio-]6-methyl-4-(3-nitrophenyl)-5-pyrimidinecarboxylic acid, methyl ester (1.14 g, 2.66 mmole) in 15 ml of dichloromethane under argon at 0°-5° C. was treated with pyridine (0.42 ml, 0.42 g, 5.32 mmole) and methanesulfonyl chloride (0.28 ml, 0.41 g, 3.57 mmole). The mixture was then allowed to stir at room temperature overnight.

Volatiles were evaporated in vacuo and the residue, dissolved in ethyl acetate, was washed with 1N hydrochloric acid (twice), water (three times), sodium bicarbonate, water and saturated brine. The aqueous fractions were back extracted with fresh ethyl acetate. The combined organic fractions were dried (magnesium sulfate) and concentrated in vacuo to give 1.36 g of an oil. Flash chromatography on 250 ml of LPS-1 silica gel and elution with 2 liters of acetone/hexane (1:4) gave 0.58 g of product.

(D) 1, 2, 3, 4-Tetrahydro-6-methyl-3-(methylsulfonyl)-4-(3-nitrophenyl) -2-thioxo-5-pyrimidinecarboxylic acid, methyl ester A solution of 1, 6-dihydro-2-[[(4-methoxyphenyl) methyl]thio]-4-methyl-1-(methylsulfonyl)-6-(3-nitrophenyl) -5-pyrimidinecarboxylic acid, methyl ester (0.57 g, 1.1 mmole) in 8 ml of dichloromethane under argon at room temperature was treated with trifluoroacetic acid (0.3 ml, 0.42 g, 3.8 mmole) and ethanethiol (0.2 ml, 0.16 g, 2.7 mmole) and allowed to react for 1 hour.

Volatiles were evaporated in vacuo and the residue was triturated with isopropyl ether overnight to give 320 mg of product, melting point 162°–166° C. This was combined with an additional 70 mg of material from a second crop and recrystallized from methanol to give 310 mg of the title product, melting point 188°–190° C. Analysis Calc'd. for $C_{14}H_{15}N_3O_6S_2$: C, 43.62; H, 3.92; N, 10.90; S, 16.64. Found: C, 43.94; , 3.94; N, 10.84; S, 16.65.

EXAMPLE 2

1, 2, 3, 4-Tetrahydro-6-methyl-4-(3-nitrophenyl)-3-(phenylsulfonyl) -2-thioxo-5-pyrimidinecarboxylic acid, ethyl ester

(A) 1, 4-Dihydro-2-[[(4-methoxyphenyl)methyl]thio]-6-methyl -4-(3-nitrophenyl)-5-pyrimidinecarboxylic acid, ethyl ester A mixture of 13.58 g of 2-(3-nitrophenyl)-methylene] -3-oxobutanoic acid, ethyl ester, 12.0 g of S-[(4-methoxyphenyl)methyl]thiopseudourea, hydrochloride and 4.18 g (0.051 mole) of sodium acetate in 90 ml of dimethylformamide was stirred and heated at 70° C. for 4 hours. After cooling, ether was added followed by washing with water, sodium bicarbonate and brine. The dried solution was evaporated to give an oil which was treated with isopropyl ether to form 18.8 g of a cream colored solid, melting point 95°–97° C.

(B) 1, 6-Dihydro-2-[[(4-methoxyphenyl)methyl]thio]-4-methyl -6-(3-nitrophenyl)-1-(phenylsulfonyl)-5-pyrimidinecarboxylic acid, ethyl ester A stirred solution of 1.5 g (0.0034 mole) of 1, 4-dihydro-2-[[(4-methoxyphenyl)methyl]thio]-6-methyl -4-(3-nitrophenyl)-5-pyrimidinecarboxylic acid, ethyl ester in 10 ml of dichloromethane containing 0.6 ml (0.0074 mole) of pyridine was treated gradually with a solution of 0.72 g (0.0041 mmole) of benzenesulfonyl chloride in 5 ml of dichloromethane. After 16 hours, dichloromethane was added and the solution was washed with water, 1N hydrochloric acid, sodium bicarbonate and brine. The dried solution was evaporated to give 2.1 g of an oil which slowly solidified. Treatment with ethyl acetate gave 0.48 g of a colorless solid, melting point 194°–196° C. (hydrochloric acid salt of 1, 4-dihydro-2-[[(4-methoxyphenyl)methyl]-thio]-6-methyl -4-(3-nitrophenyl)-5-pyrimidinecarboxylic acid, ethyl ester.

The ethyl acetate solution was concentrated and flash chromatographed using ethyl acetate/hexane (1:3) to give 1.02 g of the title compound as an oil which slowly solidified, melting point 86°–88° C. Analysis Calc'd. for $C_{28}H_{27}N_3O_7S_2$: C, 57.81; H, 4.67; N, 7.22. Found: C, 57.91; H, 4.92; N, 7.03.

(C) 1, 2, 3, 4-Tetrahydro-6-methyl-4-(3-nitrophenyl)-3-(phenylsulfonyl) -2-thioxo-5-pyrimidinecarboxylic acid, ethyl ester A solution of 0.95 g (0.0016 mole) of 1, 6-dihydro-2-[(4-methoxyphenyl)methyl]thio]-4-methyl -6-(3-nitrophenyl)-1-(phenylsulfonyl)-5pyrimidinecarboxylic acid, ethyl ester, 0.6 ml (0.0066 mole) of trifluoroacetic acid and 0.24 g (0.0037 mole) of ethanethiol in 20 ml of dichloromethane was stirred at room temperature overnight. The solvent was evaporated and the residue (solid) was treated with isopropyl ether to give 0.68 g of the title compound as a colorless solid, melting point 162°–164° C. Analysis Calc'd. for $C_{20}H_{19}N_3O_6S_2$: C, 52.04; H, 4.14; N, 9.10; S, 13.89. Found: C, 51.77; H, 4.09; N, 8.96; S, 13.71.

EXAMPLE 3

3-(Butylsulfonyl)-1, 2, 3, 4-tetrahydro-6-methyl-4-(3-nitrophenyl) -2-thioxo-5-pyrimidinecarboxylic acid, ethyl ester

(A) 1-(Butylsulfonyl)-1, 6-dihydro-2-[[(4-methoxyphenyl) methyl]thio]-4-methyl-6-(3-nitro-phenyl)-5-methyl -4-(3-nitro-phenyl)-5-pyrimidinecarboxylic acid, ethyl ester A solution of 2.0 g (0.0045 mole) of 1, 4-dihydro-2-[[(4-methoxyphenyl)methyl]thio]-6-methyl -4-(3-nitrophenyl)-5-pyrimidinecarboxylic acid, ethyl ester (see example 2A) in 15 ml of dichloromethane containing 0.8 ml (0.0098 mole) of pyridine was cooled to -10° C. and treated slowly with a solution of 0.85 g (0.0054 mole) of 1-butanesulfonyl chloride in 5 ml of dichloromethane. The ice bath was removed after 2 hours and the reaction was stirred at room temperature for 48 hours.

The hydrochloric acid salt of 1, 4-dihydro-2[[(4-methoxyphenyl)methyl]thio]-6-methyl-4-(3-nitrophenyl) -5-pyrimidinecarboxylic acid, ethyl ester (1.12 g of colorless solid, melting point 190°–192° C.) was separated and the solvent was evaporated to an oil. In ethyl acetate, this material was washed with water, 1N hydrochloric acid, sodium bicarbonate and brine. The dried solution was evaporated to give 1.2 g of an oil. Flash chromatography using ethyl acetate/hexane (1:4) gave 0.8 g of an oil which slowly solidified, melting point 66°–68° C. Analysis Calc'd. for $C_{26}H_{31}N_3O_7S_2C$, 55.59; H, 5.56; N, 7.48. Found: C, 56.33; H, 5.67; N, 7.07.

(B) 3-(Butylsulfonyl)-1, 2, 3, 4-tetrahydro-6-methyl4-(3-nitrophenyl)-2-thioxo-5-pyrimidinecarboxylic acid, ethyl ester A solution of 0.80 g (0.0014 mole) of 1-(Butylsulfonyl)-1, 6-dihydro-2-[[(4-methoxyphenyl) methyl]thio]-4-methyl-6-(3-nitrophenyl)-5-pyrimidinecarboxylic acid, ethyl ester, 0.52 ml (0.0057 mole) of trifluoroacetic acid and 0.21 g (0.0032 mole) of ethanethiol in 15 ml of dichloromethane was stirred at room temperature for 24 hours. The solvent was evaporated, and the residue was flash chromatographed using ethyl acetate/ hexane (1:4) to give an oil which solidified very slowly. Trituration with isopropyl ether gave 0.33 g of the title compound as a colorless solid, melting point 118°–120° C. Analysis Calc'd. for $C_{18}H_{23}N_3O_6S_2$: C, 48.96; H, 5.25; N, 9.51; S, 14.52. Found: C, 48.99; H, 5.42; N, 9.32; S, 14.48.

EXAMPLE 4

1, 2, 3, 4-Tetrahydro-6-methyl-3-(methylsulfonyl)-4-(3-nitrophenyl) -2-thioxo-5-pyrimidinecarboxylic acid, ethyl ester

(A) 1, 6-Dihydro-2-[[(4-methoxyphenyl)methyl]thio]-4-methyl -1-(methylsulfonyl)-6-(3-nitrophenyl)-5-pyrimidinecarboxylic acid, ethyl ester A solution of 2.0 g (0.0045 mole) of 1, 4-dihydro-2-[[(4-methoxyphenyl)methyl]thio]6-methyl-4-(3-nitrophenyl) -5-pyrimidinecarboxylic acid, ethyl ester (see example 2A) in 15 ml of dichloromethane containing 0.71 g (0.0090 mole) of pyridine was cooled to -10°

C. and treated slowly with a solution of 0.62 g (0.0054 mole) of methanesulfonyl chloride in 5 ml of dichloromethane. After stirring at room temperature overnight, a small amount of the hydrochloric acid salt of 1, 4-dihydro-2-[[(4-methoxyphenyl)methyl]thio]-6-methyl-4-(3-nitrophenyl)-5-pyrimidinecarboxylic acid, ethyl ester had precipitated. After filtration, additional dichloromethane was added and the solution was washed with water, 1N hydrochloric acid, sodium bicarbonate and brine. The dried solution was evaporated and the residue was flash chromatographed using dichloromethane to give 2.0 g of an oil.

(B) 1, 2, 3, 4-Tetrahydro-6-methyl-3-(methylsulfonyl)-4-(3-nitrophenyl) -2-thioxo-5-pyrimidinecarboxylic acid, ethyl ester A solution of 2.0 g (0.0038 mole) of 1, 6-dihydro-2-[[(4-methoxyphenyl)methyl]thio]-4-(methylsulfonyl) -6-(3-nitrophenyl)-5-pyrimidinecarboxylic acid, ethyl ester, 1.4 ml (0.0153 mole) of trifluoroacetic acid and 0.57 g (0.0086 mole) of ethanethiol in 20 ml of dichloromethane was stirred at room temperature for 40 hours and heated to reflux for 8 hours. The mixture was cooled and filtered to give 1.05 g of the compound as a colorless solid, melting point 161°–163° C. Analysis Calc'd. for $C_{15}H_{17}N_3O_6S_2$: C, 45.10; H, 4.28; N, 10.51; S, 16.05. Found: C, 45.03; H, 4.17; N, 10.42; S, 16.04.

EXAMPLE 5

1, 2, 3, 6-Tetrahydro-4-methyl-1-(methylsulfonyl)-5-(3-nitrophenyl) -2-oxo-5-pyrimidinecarboxylic acid, ethyl ester (A) 1, 4-Dihydro-2-methoxy-6-methyl-4-(3-nitrophenyl) -5-pyrimidinecarboxylic acid, ethyl ester A reaction mixture containing 2-[(3-nitrophenyl)methylene]-3-oxobutanoic acid, ethyl ester (2.62 g, 10.0 mmole), O-methylpseudourea hydrogen sulfate (1.72 g, 10.0 mmole), and sodium bicarbonate (2.52 g, 30.0 mmole) in dimethylformamide (7 ml) was heated at 65°–70° C. for 16 hours. The reaction mixture was allowed to cool to room temperature, diluted with ethyl acetate, and filtered. The filtrate was washed with water and brine, and then dried over anhydrous magnesium sulfate. Evaporation of the solvent gave a yellow oil which was purified by flash chromatography (5% ethyl acetate in dichloromethane). The resulting foam was crystallized from isopropyl ether/hexanes to provide 2.41 g of 1, 4-dihydro-2-methoxy-6-methyl -4-(3-nitrophenyl)-5-pyrimidinecarboxylic acid, ethyl ester as a colorless crystalline product; melting point 103.5°–105° C. Analysis Calc'd. for $C_{15}H_{17}N_3O_5$:
C, 56.42; H, 5.37; N, 13.16. Found: C, 56.52; H, 5.35; N, 13.03.

(B) 1, 2, 3, 6-Tetrahydro-4-methyl-1-(methylsulfonyl)-5-(3-nitrophenyl) -2-oxo-5-pyrimidinecarboxylic acid, ethyl ester A solution of 1, 4-dihydro-2-methoxy-6-methyl-4-(3-nitrophenyl) -5-pyrimidinecarboxylic acid, ethyl ester (2.00 g, 6.26 mmol), pyridine (2.5 ml, 31 mmol), and 4-dimethylaminopyridine (36 mg, 0.3 mmol) in distilled dichloromethane in an ice bath under argon was treated via syringe with distilled methanesulfonyl chloride (0.63 ml, 8.14 mmol). After five minutes, the ice bath was removed, and the reaction was stirred at room temperature overnight. The mixture was then evaporated. The residue was taken up in tetrahydrofuran (10 ml) and methanol (20 ml) and the resulting suspension was treated with 1N hydrochloric acid (8 ml) and 5N hydrochloric acid (2 ml). After stirring for 2.0 hours at room temperature, the reaction was quenched with sodium bicarbonate and extracted with ethyl acetate. The organic phase was then washed with saturated sodium chloride. Flash chromatography (ethyl acetate/hexanes (1:1))and crystallization from dichloromethane/isopropyl ether gave the title compound as white crystals (605 mg), melting point 175°–176° C. Analysis Calc'd. for $C_{15}H_{17}N_3O_7S$ : C, 46.99; H, 4.47; N, 10.96; S, 8.36. Found: C, 47.12; H, 4.39; N, 10.55; S, 8.17.

EXAMPLE 6

1, 2, 3, 6-Tetrahydro-4-methyl-6-(3-nitrophenyl)-2-oxo -1-(phenylsulfonyl)-5-pyrimidinecarboxylic acid, ethyl ester (A) 1, 2, 3, 6-Tetrahydro-4-methyl-6-(3-nitrophenyl)-2-methoxy -1-(phenylsulfonyl)-5-pyrimidinecarboxylic acid, ethyl ester A solution of 1, 4-dihydro-2-methoxy-6-methyl-4-(3-nitrophenyl) -5-pyrimidinecarboxylic acid, ethyl ester (3.19 g, 10.0 mmole; see Example 5A) and distilled triethylamine (4.18 ml, 30.0 mmol) in distilled dichloromethane (20 ml) in an ice bath under argon was treated dropwise via syringe with benzenesulfonyl chloride (1.53 ml, 12.0 mmol). The reaction was then stirred at room temperature overnight; and then over the weekend. The mixture was partitioned between ethyl acetate and water. The organic phase was washed with saturated sodium chloride and flash chromatographed to give the title compound as a light brown oil (2.94 g).

(B) 1, 2, 3, 6-Tetrahydro-4-methyl-6-(3-nitrophenyl)-2-oxo -1-(phenylsulfonyl)-5-pyrimidinecarboxylic acid, ethyl ester A solution of 1, 2, 3, 6-tetrahydro-4-methyl-6-(3-nitrophenyl)-2-methoxy-1-(phenylsulfonyl)-5 -pyrimidinecarboxylic acid, ethyl ester (1.49 g, 3.24 mmol) in tetrahydrofuran-methanol (20 ml each) was treated with 5N hydrochloric acid (5.0 ml) and stirred at room temperature overnight. The reaction mixture was evaporated and partitioned between ethyl acetate and water. The organic phase was washed with saturated sodium bicarbonate and saturated sodium chloride. Flash chromatography (acetone/hexanes (1:5)) and crystallization from dichloromethane/isopropyl ether gave the title compound as white crystals (589 mg), melting point 187°–188° C. 3 Analysis Calc'd. for $C_{20}H_{19}N_3O_7S$: C, 53.93; H, 4.30; N, 9.43; S, 7.20. Found: C, 53.71; H, 4.19; N, 9.27; S, 7.13.

Additional compounds falling within the scope of this invention are:

6-(2, 3-dichlorophenyl)-1, 2, 3, 4-tetrahydro-4-methyl -2-oxo-1-(phenylsulfonyl)-5-pyrimidinecarboxylic acid, ethyl ester 1-(1-butylsulfonyl)-1, 2, 3, 4-tetrahydro-4-methyl -6-(3-nitrophenyl)-2-oxo-5-pyrimidinecarboxylic acid, 2-(dimethylamino)ethyl ester 1, 2, 3, 4-tetrahydro-4-methyl-1-(methylsulfonyl)-6-(2-nitrophenyl)-2-oxo-5-pyrimidinecarboxylic acid, ethyl ester 1, 2, 3, 4-tetrahydro-4-methyl-1-[3-[(phenylmethyl)(methyl)amino]propyl]sulfonyl]-6-(3-nitrophenyl) -2-oxo-5-pyrimidinecarboxylic acid, 1-methylethyl ester.

1, 2, 3, 4-tetrahydro-4-methyl-1-[[3-[4-(phenylmethyl)-1-piperazinyl]propyl]sulfonyl]-6-(3-nitrophenyl)-2-oxo-5-pyrimidinecarboxylic acid, ethyl ester 1, 2, 3, 4-tetrahydro-4-methyl-1-[[3-(dimethylamino)-propyl]sulfonyl]-2-oxo-6-[2-(trifluoromethyl) phenyl]-5-pyrimidinecarboxylic acid, ethyl ester 1, 2, 3, 4-tetrahydro-4-methyl-2-oxo-1-[(phenylmethyl)sulfonyl]-6-[2(methylthio)-3-pyridyl]-5-pyrimidinecarboxylic acid, ethyl ester 6-(4-benzoxadiazolyl)-1, 2, 3, 4-tetrahydro-4-methyl-2-oxo-1-(phenylsulfonyl)-5-pyrimidine-carboxylic acid, 2-[(phenylmethyl)(methyl)amino]ethyl ester 1-(1-butylsulfonyl)-6-(2-chloro-3-nitrophenyl) -1, 2, 3, 4-tetrahydro-4-methyl-2-oxo-5-pyrimidinecarboxylic acid, 1-(phenylmethyl)-4-piperidinyl ester 6-(2, 3-dichlorophenyl)-1, 2, 3, 4-tetrahydro-4-methyl-1-(phenylsulfonyl)-2-thioxo-5-pyrimidinecarboxylic acid, ethyl ester 1-(1-butylsulfonyl)-1, 2, 3, 4-tetrahydro-4-methyl -6-(3-nitrophenyl)-2-thioxo-5-pyrimidinecarboxylic, 2-(dimethylamino)ethyl ester 1, 2, 3, 4-tetrahydro-4-methyl-1-(methylsulfonyl)-6-(2-nitrophenyl)-2-thioxo-5-pyrimidine carboxylic acid, ethyl ester 1, 2, 3, 4-tetrahydro-4-methyl-1-[3-[(phenylmethyl) (methyl)amino]propyl]sulfonyl]-6-(3-nitrophenyl)-2-thioxo-5-pyrimidinecarboxylic acid, 1-methylethyl ester 1, 2, 3, 4-tetrahydro-4-methyl-1-[[3-[4-(phenylmethyl)-1-piperazinyl]propyl]sulfonyl]-6-(3-nitrophenyl) -2-thioxo-5-pyrimidinecarboxylic acid, ethyl ester 1, 2, 3, 4-tetrahydro-4-methyl-1-[[3-(dimethylamino) propyl]sulfonyl]-2-thioxo-6-[2-(trifluorometyl) phenyl]-5-pyrimidinecarboxylic acid, ethyl ester 1, 2, 3, 4-tetrahydro-4-methyl-2-thioxo-1-[(phenylmethyl)sulfonyl]-6-[2-(methylthio)-3-pyridyl]-5-pyridyl]-5-pyrimidinecarboxylic acid, ethyl ester 6-(4-benzoxadiazolyl)-1, 2, 3, 4-tetrahydro4-methyl -2-thioxo-1-(phenylsulfonyl)-5-pyrimidine-carboxylic acid, 2-[(phenylmethyl)(methyl)amino], ethyl ester 1-(1-butylsulfonyl)-6-(2-chloro-3-nitrophenyl) -1, 2, 3, 4-tetrahydro-4-methyl-2-thioxo-5-pyrimidinecarboxylic acid, 1-(phenylmethyl)-4-piperidinyl ester

What is claimed is:

1. A compound having the formula

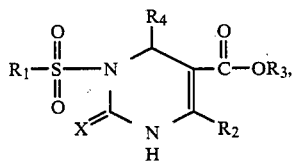

or a pharmaceutically acceptable salt thereof wherein
X is oxygen or sulfur;
$R_1$ is alkyl, cycloalkyl, aryl, [heterocyclo,]—$(CH_2)_n$—$Y_1$, or halo substituted alkyl;
$R_2$ is hydrogen, alkyl, alkenyl, alkynyl, cycloalkyl, aryl, —$(CH_2)_n$—$Y_1$, or halo substituted alkyl;

$R_3$ is hydrogen, alkyl, cycloalkyl, aryl, [heterocyclo,-]—$(CH_2)_n$—$Y_2$, —$(CH_2)_p$—$Y_3$, or halo substituted alkyl;
$R_4$ is aryl [or heterocyclo];
$Y_1$ is cycloalkyl, aryl, [heterocyclo,] hydroxyl, alkoxy, aryl—$(CH_2)_m$—O—mercapto, alkylthio, aryl—$(CH_2)_m$—S—, (substituted amino)—$\overset{O}{\underset{\|}{C}}$—, carboxyl, alkoxycarbonyl, alkyl—$\overset{O}{\underset{\|}{C}}$—, aryl—$(CH_2)_m$—$\overset{O}{\underset{\|}{C}}$—, alkyl—$\overset{O}{\underset{\|}{C}}$—O— or aryl—$(CH_2)_m$—$\overset{O}{\underset{\|}{C}}$—O—;

$Y_2$ is cycloalkyl, aryl, carbamoyl, (substituted amino)—$\overset{O}{\underset{\|}{C}}$—, carboxyl, alkoxycarbonyl, alkyl—$\overset{O}{\underset{\|}{C}}$—, or aryl—$(CH_2)_m$—$\overset{O}{\underset{\|}{C}}$—

$Y_3$ is hydroxyl, alkoxy, aryl—$(CH_2)_m$—O—, mercapto, alkylthio, aryl—$(CH_2)_m$—S—, alkyl—$\overset{O}{\underset{\|}{C}}$—O—, aryl—$(CH_2)_m$—$\overset{O}{\underset{\|}{C}}$—O—, amino, or substituted amino;
m is O or an integer of 1 to 6;
n is an integer of 1 to 6; and
p is an integer of 2 to 6; wherein
the term "aryl" refers to phenyl or phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups;
the term "cycloalkyl" refers to cycloalkyl groups having 3, 4, 5, 6 7 carbon atoms; and
the term "substituted amino" refers to a group of the formula —$NZ_1Z_2$ wherein $Z_1$ is hydrogen, alkyl, or aryl—$(CH_2)_m$—and $Z_2$ is alkyl or aryl—$(CH_2)_m$—.

2. A compound in accordance with claim 1 wherein X is oxygen.
3. A compound in accordance with claim 1 wherein X is sulfur.
4. A compound in accordance with claim 2 wherein $R_2$ is alkyl.
5. A compound in accordance with claim 3 wherein $R_2$ is alkyl.
6. A compound in accordance with claim 2 wherein $R_3$ is alkyl.
7. A compound in accordance with claim 3 wherein $R_3$ is alkyl.
8. A compound in accordance with claim 2 wherein $R_4$ is 3-nitrophenyl.
9. A compound in accordance with claim 3 wherein $R_4$ is 3-nitrophenyl.
10. A compound in accordance with claim 1 wherein $R_1$ is alkyl.
11. A compound in accordance with claim 1 wherein $R_1$ is cycloalkyl having 3, 4, 5, 6 or 7 carbon atoms.
12. A compound in accordance with claim 1 wherein $R_1$ is aryl.

13. A compound in accordance with claim 1 wherein $R_1$ is —$(CH_2)_n$—$Y_1$.

14. A compound in accordance with claim 1 wherein $R_1$ is halo-substituted alkyl.

15. A compound in accordance with claim 1 wherein X is sulfur, $R_2$ is methyl, $R_3$ is ethyl and $R_4$ is 3-nitrophenyl.

16. The compound in accordance with claim 1, 1, 2, 3, 4-tetrahydro-6-methyl-3-(methylsulfonyl)-4-(3-nitrophenyl) -2-thioxo-5-pyrimidinecarboxylic acid, methyl ester.

17. The compound in accordance with claim 1, 1, 2, 3, 4-tetrahydro-6-methyl-4-(3-nitrophenyl)-3-(phenylsulfonyl) -2-thioxo-5-pyrimidinecarboxylic acid, ethyl ester.

18. The compound in accordance with claim 1, 3-(butylsulfonyl)-1, 2, 3, 4-tetrahydro-6-methyl-4-(3-nitrophenyl) -2-thioxo-5-pyrimidinecarboxylic acid, ethyl ester.

19. The compound in accordance with claim 1, 1, 2, 3, 4-tetrahydro-6-methyl-3-(methylsulfonyl)-4-(3-nitrophenyl) -2-thioxo-5-pyrimidinecarboxylic acid, ethyl ester.

20. The compound in accordance with claim 1, 1, 2, 3, 6-tetrahydro-4-methyl-1-(methylsulfonyl)-5-(3-nitrophenyl) -2-oxo-5-pyrimidinecarboxylic acid, ethyl ester.

21. A method of lowering blood pressure in a mammalian host in need thereof, which comprises administering to said host an effective amount of a compound having the formula

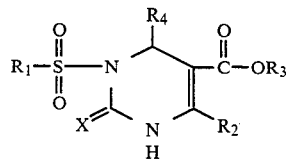

or a pharmaceutically acceptable salt thereof wherein
X is oxygen or sulfur;
$R_1$ is alkyl, cycloalkyl, aryl, —$(CH_2)_n$—$Y_1$, or halo substituted alkyl;
$R_2$ is hydrogen, alkyl, alkenyl, alkynyl, cycloalkyl, aryl, —$(CH_2)_n$—$Y_1$, or halo substituted alkyl;
$R_3$ is hydrogen, alkyl, cycloalkyl, aryl, —$(CH_2)_n$—$Y_2$, —$(CH_2)_p$—$Y_3$, or halo substituted alkyl;
$R_4$ is aryl;
$Y_1$ is cycloalkyl, aryl, hydroxyl, alkoxy, aryl—$(CH_2)_m$—O—, mercapto, alkylthio, aryl—$(CH_2)_m$—S—, amino, substituted amino, carbamoyl, $$\text{(substituted amino)}-\overset{\overset{O}{\|}}{C}-, \text{ carboxyl, alkoxycarbonyl, alkyl}-\overset{\overset{O}{\|}}{C}-,$$

$$\text{aryl}-(CH_2)_m-\overset{\overset{O}{\|}}{C}-, \text{ alkyl}-\overset{\overset{O}{\|}}{C}-O- \text{ or aryl}-(CH_2)_m-\overset{\overset{O}{\|}}{C}-O-;$$

$Y_2$ is cycloalkyl, aryl, carbamoyl $$\text{(substituted amino)}-\overset{\overset{O}{\|}}{C}-, \text{ carboxyl, alkoxycarbonyl,}$$

$$\text{alkyl}-\overset{\overset{O}{\|}}{C}-, \text{ or aryl}-(CH_2)_m-\overset{\overset{O}{\|}}{C}-$$

$Y_3$ is hydroxyl, alkoxy, aryl—$(CH_2)_m$—O—, mercapto, alkylthio, aryl—$(CH_2)_m$—S—, $$\text{alkyl}-\overset{\overset{O}{\|}}{C}-O-, \text{ aryl}-(CH_2)_m-\overset{\overset{O}{\|}}{C}-O-,$$

amino, or substituted amino;
m is 0 or an integer of 1 to 6;
n is an integer of 1 to 6; and
p is an integer of 2 to 6; wherein
the term "aryl" refers to phenyl or phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups;
the term "cycloalkyl" refers to cycloalkyl groups having 3, 4, 5, 6 or 7 carbon atoms; and
the term "substituted amino" refers to a group of the formula —$NZ_1Z_2$ wherein $Z_1$ is hydrogen, alkyl, or aryl—$(CH_2)_m$— and $Z_2$ is alkyl or aryl—$(CH_2)_m$—.

* * * * *

UNITED STATES PATENT AND TRADEMARK OFFICE
CERTIFICATE OF CORRECTION

PATENT NO. : 4,684,656

DATED : August 4, 1987

INVENTOR(S) : Karnail Atwal

It is certified that error appears in the above-identified patent and that said Letters Patent is hereby corrected as shown below:

```
In column 11, line 65, "[heterocyclo,]" should be deleted.
In column 12, line 1, "[heterocyclo,-" should be deleted.
In column 12, line 2, "]" should be deleted.
In column 12, line 4, "[or heterocyclo]" should be deleted.
In column 12, line 5, "[heterocyclo,]" should be deleted.
In column 12, line 7, after ")m-S-," insert --amino,
substituted amino, carbamoyl,--
In column 12, line 23, insert --;-- at end of line.
In column 12, line 42, "67" should read --6 or 7--.
```

Signed and Sealed this

Eighteenth Day of October, 1988

Attest:

DONALD J. QUIGG

*Attesting Officer*     *Commissioner of Patents and Trademarks*